United States Patent [19]

Schreiber et al.

[11] Patent Number: 4,599,331

[45] Date of Patent: Jul. 8, 1986

[54] ETIANIC ACIDS AS ANTIANGIOGENICS

[75] Inventors: Alain B. Schreiber, Sunnyvale; William J. Kowalski; Stefan H. Unger, both of Palo Alto, all of Calif.

[73] Assignee: Syntex (U.S.A.) Inc., Palo Alto, Calif.

[21] Appl. No.: 685,568

[22] Filed: Dec. 24, 1984

[51] Int. Cl.[4] .............................................. A61K 31/56
[52] U.S. Cl. .................................. 514/179; 260/397.1
[58] Field of Search ...................... 260/397.1; 514/179

[56] References Cited

U.S. PATENT DOCUMENTS 4,198,403  4/1980  Alvarez ........................... 260/397.1
4,310,466  1/1982  Edwards .......................... 260/397.1

Primary Examiner—Elbert L. Roberts
Attorney, Agent, or Firm—Charles L. Hartman; Tom M. Moran; Alan M. Krubiner

[57] ABSTRACT

This invention provides a method for inhibiting angiogenesis in mammals. A pharmaceutically acceptable formulation containing a compound of the formula

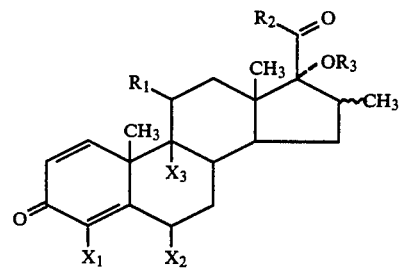

where $X_1$ $X_2$ and $X_3$ are H, Cl, or F and $X_3$ must be H if the substituent of $R_1$ is $\alpha$OH;

$R^1$ is chosen from the group consisting of hydroxyl and hydrogen;

$R_2$ is chosen from the group of alkyloxy or thioalkyls wherein said alkyls have less than 5 carbon atoms $R_3$ is H or an alkyl having less than 6 carbon atoms, is administered to the mammal having undesirable angiogenesis.

The wavy line at C-16 refers to either $\alpha$ or $\beta$.

10 Claims, No Drawings

ETIANIC ACIDS AS ANTIANGIOGENICS

BACKGROUND OF THE INVENTION

This invention relates to the use of novel steroid compounds, particularly to the use of compounds of the class of etianic acids, for inhibition of blood vessel formation. Certain etianic acids and esters derived therefrom can inhibit blood vessel formation, and can be used in treating solid tumor growth, ophthalmic retinopathies including diabetic, and granulomatous disease, and as a contraceptive, as well.

"Angiogenesis" is the term used to describe new blood vessel formation. Angiogenesis is a feature of many diseases and physiological conditions, for example, ophthalmic retinopathies, granulomatous disease, and solid tumor growth, as well as wound healing and corpus luteum formation. Folkman discusses angiogenesis in a general way in *Ann. N.Y. Acad. Sci.* 1982, p. 212.

Conditions characterized by angiogenesis may be treated by inhibiting angiogenesis, if the treatment has few side effects. For example, angiogenesis accompanies most solid tumor growth. The prevention of further angiogenesis can inhibit further tumor growth in some cases. As another example, preventing angiogenesis is an effective means of contraception in mammals.

Folkman has demonstrated both that angiogenesis is necessary for tumor growth, and that tumor growth stops if angiogenesis is inhibited. See *Science,* 221, Aug. 1983, p. 719-725. He reported that if angiogenesis was inhibited by a combination of heparin, or heparin fragments, and cortisone, tumor growth could be stopped and even reversed. He always administered both heparin and a glucocorticoid steroid to achieve the anti-angiogenic effect. One disadvantage that he has recognized is that not all heparins give identical results. (See *Science* 221 at p. 722) And, in one case, the heparin that gave the best anti-angiogenic activity was removed from the market during the pendancy of the study. Later, he reported the successful use of hydrocortisone and heparin to inhibit angiogenesis in *The Third International Symposium on the Biology of Vascular Endothelial Cell*, at Cambridge, Mass. June 25-29, 1984.

It would be advantageous to find a class of steroid compounds that are anti-angiogenic, that do not have any other biological effects, particularly severe glucocorticoid effects. The applicant has found that etianic acids and their esters do show anti-angiogenic effects.

SUMMARY OF THE INVENTION

This invention provides a method for inhibiting angiogenesis in mammals. A pharmaceutically acceptable formulation containing a compound of the formula

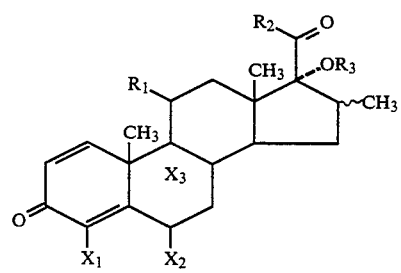

FORMULA 1 where $X_1$ $X_2$ and $X_3$ are H, Cl, or F,
where $X_3$ must be H if the substituent of $R_1$ is $\alpha$OH;
$R_1$ is chosen from the group consisting of hydroxyl or hydrogen
$R_2$ is chosen from the group of alkyloxy or thioalkyls wherein said alkyls have less than 5 carbon atoms;
$R_3$ is H or an alkyl having less than 6 carbon atoms, is administered to the animal having undesirable angiogenesis.

The wavy line at C-16 refers to either $\alpha$ or $\beta$.

"Inhibiting angiogenesis" as used in the context of this invention means preventing further vascular development or slowing further development of vascularization. The longer term use of the anti-angiogenic etianic esters of this invention can result in the destruction of vessels due to angiogenesis already present, and this phenomenon is also included in the term.

Unless a specific formula is intended, the term "etianic acid ester" as used herein will refer to the generic class of compounds of Formula 1. Examples of such etianic acid esters are shown in U.S. Pat. Nos. 4,198,336, 4,278,699, 4,261,986, 4,198,404, 4,198,403, 4,261,984, 4,187,301, 4,188,385 and 4,263,289.

DETAILED DESCRIPTION

As an untreated tumor grows, blood vessels in and around it will typically proliferate. One can easily visually determine which blood vessels are due to tumor related angiogenesis, because these vessels are particularly tortuous, and, in advanced cases, are characterized by localized blood leakage and hemorrhage. The administration of etianic acids inhibits the vascularization that normally accompanies tumor growth and as a result, the tumor fails to grow. If its growth is prevented long enough, the tumor may regress.

Other diseases, for example ophthalmic retinopathies and granulomatous diseases can be treated similarly. Etianic esters are useful as contraceptives, since they can prevent formation of the corpus luteum required for embryonal development.

Effective systemic administration includes oral administration, and subcutaneous or intraperitoneal injection. The present invention is also useful for those localized diseases, such as skin tumors and the like, where topical administration is possible.

Depending on the intended mode of administration, the compositions used may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical carrier or excipient and an active compound of Formula I and, in addition, may include other medicinal agents, pharmaceutical agents, carriers, adjuvants, and the like.

For solid compositions, conventional non-toxic solid carriers that may be used include, for example, pharmaceutical grades of mannitol, lactose, starch, magnesium stearate, sodium saccharin, talcum, cellulose, glucose, sucrose, magnesium carbonate, and the like. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound(s) in an amount effective to alleviate the symptoms of the subject being treated.

For the compounds of formula I, either oral or topical administration is preferred depending on the nature of the disorder being treated.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 1%–95% active ingredient, preferably 25–70%.

For topical administration, these compositions comprise an effective amount of a compound of this class in a mixture with a pharmaceutically acceptable non-toxic carrier. A suitable range of composition would be 0.1%–10% active ingredient, and the balance carrier, preferably 1-2% active ingredient.

Some members of the class of etianic acids are known to have glucocorticoid effects, but there is no relationship between anti-angiogenic activity and glucocorticoid activity. Some compounds known to be powerful glucocorticoids have little or no anti-angiogenic activity and some compounds known to have no glucocorticoid activity have anti-angiogenic activity. All of the etianic esters, as defined above, have at least some anti-angiogenic activity.

The ideal compound would have high anti-angiogenic efficiency, but no glucocorticoid, or other steroid or other undesirable side effects. To screen the series of etianic esters each was tested for glucocorticoid activity using a binding competition test, the tyrosine amino transferase induction test, and the alkaline phosphatase induction test.

Each compound of the series was also tested for anti-angiogenic activity by an in vivo test that measured vascularization in a hamster's cheek pouch in response to either an angiogenic polypeptide growth factor, epidermal growth factor (EGF) or an induced timer. The results of all the tests, for the ester and thio ester subclasses of etianic esters series, are tabulated in Tables 1, 2, and 3.

EXAMPLE 1

In this example, the affinities of test compounds for the glucocorticoid receptor were determined by competition for $^3$H-dexamethasone (DEX) binding sites in cytosols from tissue culture cells.

LE II (mouse lung capillary endothelial) or HTC (rat hepatoma) cells were grown in Dulbecco's modified Eagle's (DMEM) medium plus 10% fetal calf serum (FCS), in 150 cm$^2$ T-flasks. Approximately 20 flasks of LE II cells or 10 flasks of HTC cells were needed for a 60–80 sample assay.

Cell monolayers were washed 3 times with Phosphate Buffered Saline (PBS) and harvested by scraping with a rubber policeman into an ice-cold sonication buffer of 0.25M sucrose; 10 mM Tris-HCl, pH 7.4; 5 mM ethylenediaminetetraacetic acid (EDTA); 5 mM dithiothereitol; and 10 mM sodium molybdate. All subsequent steps were performed at 4° C. The cells were pooled into a final volume of 8–12 mls, broken by sonication for 45 seconds with the microtip of a Branson sonifier at setting #3 and the residue was then centrifuged at 100,000 X g for 30 minutes with a Beckman L8-50, Ti50 rotor, at 40,000 rpm. Individual portions of the cytosol were incubated with 25 nM $^3$H-DEX, either with or without unlabeled test compounds, at concentrations between 0.25–250 nM. Incubations were performed in a final volume of 1 ml in 1.5 ml Eppendorf centrifuge tubes for 3 hours on ice.

Separation of free from protein-bound $^3$H-DEX was accomplished by chromatography on Sephadex G-50 minicolumns. Fine Sephadex G-50 gel was swollen and equilibrated against column buffer of 100 mM Tris-HCl, pH 7.8; and 3 mM CaCl$_2$. Columns were poured to a final packed volume of 4.5 ml in 5 ml plastic disposable pipets.

The packed columns were then drained of buffer and the 1 ml incubated samples were applied to each. The samples were washed into the columns with 0.5 ml of column buffer, and the exclusion volumes containing the protein peaks were eluted with another 1 ml of column buffer and collected. Aliquots of 750 μl of Biorad protein reagent were diluted 1:5 in H$_2$O. OD$_{630nm}$ reading were compared with those obtained for a bovine serum albumin standard curve. See the BHTC and BLE11 Columns in Tables 1 and 2.

Final values are expressed as fmoles $^3$H-DEX bound per mg of protein. Scatchard analyses show that LE II cells bind approximately 500 fmoles of $^3$H-DEX per mg at saturation, with an equilibrium dissociation constant of $8 \times 10^{-9}$M; while HTC cells bind about 1100 fmoles of $^3$H-DEX per mg protein at saturation, with an equilibrium dissociation constant of $4 \times 10^{-9}$M.

Results are expressed in Tables 1 and 2 as the concentration required for 50% inhibition (IC)$_{50}$ in displacement experiments.

EXAMPLE 2

In this example, tyrosine aminotransferase (TAT) activity was determined by a spectrophotometric assay. This enzyme catalyzes the conversion of tyrosine to p-hydroxyphenylpyruvate. This example is a standard in vitro test for glucocorticoid activity.

Addition of base caused the conversion of p-hydroxyphenylpyruvate to p-hydroxybenzaldehyde, which was quantitatively measured by absorbance at 331 nm. HTC cells, the target cells for the compound tested were grown in DMEM+10% FCS. Subconfluent cell cultures were incubated with test compounds in 6 well Costar dishes for 24 or 48 hours. The cells were incubated in either serum-free DMEM or DMEM containing 10% FCS previously filtered over activated charcoal. The cells were harvested in PBS using a rubber policeman, then washed once in PBS by centrifugation and resuspended in a 0.3 ml lysis buffer of 10 mM Tris, 10 mM EDTA and 0.25M sucrose at pH 7.4. The cells were then lysed by three cycles of freeze-thawing using dry ice and a 37° C. waterbath and the cells debris was pelleted by centrifugation for 2 min at 12,000 9 in an Eppendorf centrifuge.

The supernatant was used for a protein determination using either E+K stain or BioRad protein assay kit and TAT activity. 0.1 ml TAT buffer having 50 mM $KH_2PO_4$, 1 mM EDTA, 0.1 mM Dithiothereitol (DTT), and 5 mg/ml BSA at pH 7.6 and 0.1 ml cell extract were mixed in glass tubes. A prewarmed mixture of 200 parts of a 2.3 mg/ml tyrosine solution in 0.05M phosphate buffer, 100 parts 0.125M $KH_2PO_4$, 10 parts of a 0.92 mg/ml and ketoglutarate solution and 1 part of a 0.04 mg/ml pyridoxalphosphate solution had been previously made up. 9.7 ml of the prewarmed mixture was added to each tube and allowed to react at 37° C. for 15 min. The addition of 0.1 ml 7N HOH stopped the reaction. The mixture was then immediately vortexed.

Aldehyde formation was allowed to proceed at 37° C. for 30 min. The amount of aldehyde formed was determined by UV spectroscopic means. Absorbance was read at 331 nm using a solution composed of 0.1 ml TAT buffer, 0.1 ml lysis buffer, 0.7 ml reaction mixture and 0.1 ml 7N KOH as a blank. Optical Density values are linearily corrected for protein content.

As the absolute amount of enzyme induction varies between experiments, results are expressed as percent of the maximal induction obtained with dexamethasone, which was run as a standard in each assay. Dexamethasone induces maximal TAT activity at $10^{-7}M$ with an $EC_{50} \sim 2 \times 10^{-8}M$.

In this series, compounds were assayed from $10^{-6}M$ down. Results are expressed in the TAT column of tables 1, and 2 as the induction ability of a compound as compared to dexamethasone; a compound may either be a partial inducer or a superinducer.

EXAMPLE 3

This example shows a test for alkaline phosphatase (APb) activity. This is another standard test for glucocorticoid activity.

LE II cells were grown in DMEM plus 10% FCS, at 37° C., in a 10% carbon dioxide atmosphere. Confluent monolayers of cells were trypsinized and seeded at a 1:15 dilution into 6-well Costar cluster dishes. After allowing 24 hours for attachment, the culture medium was replaced with fresh medium, either with or without the test compound. In all experiments, DEX, at concentrations of $10^{-9}$ to $10^{-6}M$, was added to some of the wells as a positive control. Preliminary experiments had shown that maximum induction of alkaline phosphatase activity by DEX was seen after 48-72 hours of incubation; for routine experiments, the cells were incubated for about 65 hours.

Cell monolayers were washed with PBS and harvested by scraping with a rubber policeman into 400 μl of a buffer of 20 mM Tris-HCl at pH 7.4; 2 mM $MgCl_2$; and 150 mM NaCl together with 1% Triton X-100. Samples were transferred into 1.5 ml Eppendorf centrifuge tubes and placed on ice. The tubes were first vortexed and then centrifuged in the Eppendorf minicentrifuge for 2 minutes. Duplicate 100 μl aliquots of supernatant were placed into 12×75 mm glass test tubes for determination of APb activity, while the rest was saved for protein determination. The alkaline phosphatase reaction was initiated by the addition to the tubes of 0.5 ml of 10 mM p-nitrophenylphosphate (Sigma) in 0.1M ethanolamine, pH 10.5. The tubes were incubated in a 37° C. water bath for between 20 to 50 minutes, depending on the activity of the samples. The APb reaction was terminated by the addition of 0.5 ml of 0.2 NaOH.

The tubes were mixed and 200 μl portions from each tube were transferred in triplicate to a 96 well microtiter plate. The $OD_{410}nm$ of each well was then determined using a Dynatech plate reader. The micromoles of product formed were determined from the molar extinction coefficient of nitrophenol at 410 nm.

Triplicate μl aliquots of the cell supernatant were transferred to 96 well microtiter plates for protein determination by a modification of the Lowry method. Fifty μl of a reaction mixture containing 0.19M $Na_2CO_3$; 0.1N NaOH; 0.7 mM sodium-potassium tartrate; and 0.8 mM $CuSO_4$ were added to each well, followed by the addition of 50 μl of 10% sodium dodecyl sulfate-5% Folin-Ciocalteu reagent (Sigma). The plates were shaken for 1 hour and then the $OD_{630}$ was determined using a Dynatech plate reader. The protein content for each sample was calculated by comparing the average $OD_{630}$ reading with those obtained for a bovine serum albumin standard curve.

The alkaline phosphatase activity of in each sample was expressed as μmoles product formed per minute per mg protein in the Alk P column of Tables 1 and 2. Results are expressed as the induction ability of a compound as compared to dexamethasone.

EXAMPLE 4

In this example, the in vivo angiogenesis inhibition activity of etianic acid esters was tested. Male Syrian Golden hamsters, weighing between 120 g and 150 g were anaesthetized by intraperitoneal (I.P.) injection of a rodent anaesthetic mixture consisting of 50 mg/kg ketamine hydrochloride, 5 mg/kg xylazine and 1 mg/kg acepromazine. The left cheek pouch of each animal was everted with a pincet and pinned down to a plexiglass-rubber stage and observed through a Zeiss stereomicroscope. 10 μg of EGF or $3 \times 10^5$ Hamster Melanoma RPM1 1846 tumor cells in 10 μl Cibachrome Blue agarose (Amicon) were injected subcutaneously in the left lower quadrant of the pouch with a Hamilton syringe.

The pouch was then reinserted and animals were kept under observation until recovered from anaesthesia.

The animals were dosed daily with one test compound, starting one day before stimulus injection and continuing until observation. The test compounds were dissolved in a minimum volume of ethanol and diluted in sterile phosphate buffer solution. Then between 0.5 and 4 mg/kg of the test compound was injected subcutaneously.

Either five days or twelve days after the EGF or tumor cell injection, animals were anaesthetized by I.P. injection of the rodent anaesthetic mixture. The pouch was everted on the stage and examined under the stereomicroscope. Pictures were taken with a 35 mm using Kodak Tungsten 50 professional films.

The following subjective scoring was used for evaluating the photographs:
0: no new vessels.
1: minimal branching of vessels in the vicinity of injection site.
2: new vessels reach injection site, area involved is minimal (<50% of area surrounding injection site).
3: many vessels reach and cross injection site, new vessels are tortuous, (>50% of area surrounding injection site).
4: "full blown", many tortuous vessels, leakages, hemorrhages, 100% of area around injection site, invasion of new vessels into non-injected areas.

In the case of the tumor, tumor size was also determined. (See Table 4)

Results are expressed as the mean of the score. The results are shown in Tables 1 and 2 are percent inhibition of HCP Stimulus. Results of a two week assay for various compounds are shown in Table 3.

TABLE 1

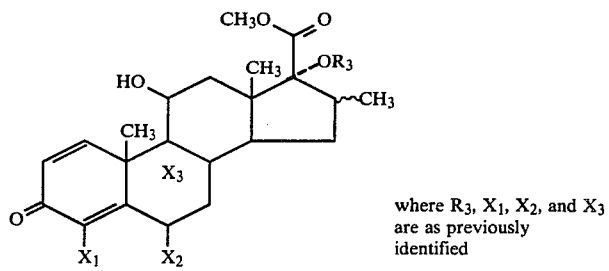

where $R_3$, $X_1$, $X_2$, and $X_3$ are as previously identified

| | $X_1$ | $X_2$ | $X_3$ | 16 | $R_3$ | $IC_{50}$ (nM) Binding HTC | $IC_{50}$ (nM) Binding LEII | Efficacy (DEX = 1) TAT | Efficacy (DEX = 1) Alk P | % Inhibition HCP Stimulus Epidermal Growth Factor | % Inhibition HCP Stimulus 1846 |
|---|---|---|---|---|---|---|---|---|---|---|---|
| 1 | H | H | F | β | PROP | 5 | 2 | 1.0 | 1.0 | 70, 77 | 40 |
| 2 | H | F | F | β | PROP | | | 0.8 | 0.9 | 100, 100 | 33, 35 |
| 3 | F | F | F | β | PROP | 15 | 15 | 1.5 | 1.0 | 95, 91 | 70, 70 |
| 4 | H | F | F | β | BUT | 0.25 | 0.25 | 1.0 | 1.7 | 100, 78 | 26 |
| 5 | H | F | F | α | FORM | | | | | −25 | |
| 6 | H | F | F | α | ACET | | | 0.7 | | 23 | |
| 7 | H | F | F | α | PROP | 4 | 0.25 | 2.0 | 1.1 | 57 | |
| 8 | F | F | F | α | PROP | 0.25 | 0.25 | 1.0 | 1.2 | 41, 58, 100, 72, 82 | 75 |
| 9 | H | F | F | α | BUT | 0.025 | 0.025 | 0.9 | 0.9 | 100 | 32 |
| 10 | H | F | F | α | VAL | 0.025 | 0.025 | 0.9 | 0.7 | 100 | 24 |

Each tabulate number is the result of tests with six animals. These show independent results, each the average of six animals.

In this table PROP refers to propionate, BUT to butyrate, VAL to valerate, and FORM refers to formate.

TABLE 2

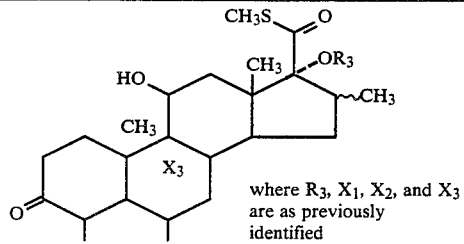

where $R_3$, $X_1$, $X_2$, and $X_3$ are as previously identified

| | $X_1$ | $X_2$ | $X_3$ | 16 | $R_3$ | Efficacy (DEX = 1) TAT | HCP[a] % Inhibition Stimulus EGF | 1846 |
|---|---|---|---|---|---|---|---|---|
| 11 | H | F | F | β | PROP | 1.4 | 100 | 28 |

TABLE 2-continued

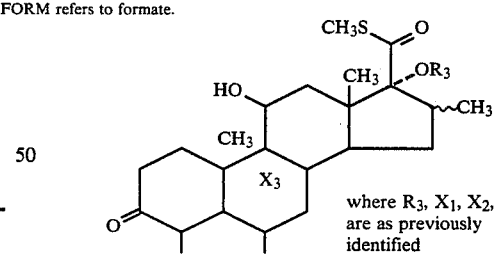

where $R_3$, $X_1$, $X_2$, and $X_3$ are as previously identified

| | $X_1$ | $X_2$ | $X_3$ | 16 | $R_3$ | Efficacy (DEX = 1) TAT | HCP[a] % Inhibition Stimulus EGF | 1846 |
|---|---|---|---|---|---|---|---|---|
| 12 | H | H | F | β | BUT | 1.3 | 37 | |
| 13 | H | F | F | β | BUT | 0.9 | 94, 84 | 40, 53, 45 |
| 14 | H | F | F | β | VAL | 0.6 | 22, 42 | 16 |
| 15 | H | H | F | α | PROP | | 30 | |
| 16 | H | F | F | α | PROP | 1.2 | 46 | 25, 35 |
| 17 | F | F | F | α | PROP | | | |
| 18 | H | F | F | α | BUT | 1.3 | | 16 |

[a]Compounds were given daily at 0.4 mg/kg.

In this table PROP refers to propionate, BUT to butyrate, and VAL to valerate.

TABLE 3

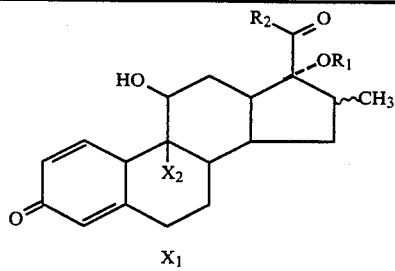

Inhibition of tumor growth (2 week assay)

| No. | $X_1$ | $X_2$ | $C_{16}$ | $R_1$ | $R_2$ | dose (mg/kg) | Angiogenesis score | % Inh. | Tumor area Mn (mm²) | % |
|---|---|---|---|---|---|---|---|---|---|---|
| [A] | None | | | | | | 3.1 | 0 | 40.7 ± 16.2 | 0 |
| 13 | F | F | β | butyrate | SCH₃ | 0.8 | 1.8 | 42 | 9.1 ± 3 | 78 |
| 9 | F | F | α | butyrate | OCH₃ | 0.8 | 2.2 | 29 | 5.7 ± 5.9 | 86 |
| 10 | F | F | α | valerate | OCH₃ | 0.8 | 2.4 | 23 | 22.5 ± 13.7 | 45 |
| [B] | None | | | | | | 2.9 | 0 | 27.5 ± 15.3 | 0 |
| 2 | F | F | β | propionate | OCH₃ | 0.8 | 1.9 | 35 | 11.6 ± 10.3 | 58 |

What is claimed is:

1. A method for inhibiting angiogenesis in animals comprising administering a pharmaceutically acceptable formulation containing a compound of the formula

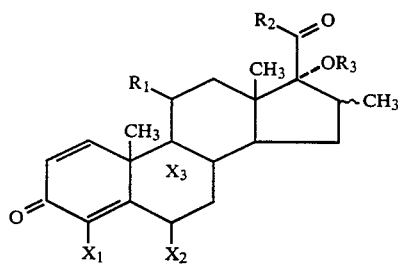

where $X_1$, $X_2$ and $X_3$ can be the same or different and can be hydrogen, fluorine and chlorine;

$R_1$ is chosen from the group consisting of hydrogen and hydroxyl;

$R_2$ is chosen from the group consisting hydrogen, methoxy and thiomethyl; and $R_3$ is chosen from the group consisting of alkyl groups having less than 6 carbon atoms.

2. The method of claim 1 wherein said compound includes those compounds having $R_1$ as hydroxyl, and $R_2$ as methoxy.

3. The method of claim 2 wherein said compound includes those compounds having $R_3$ as propionate.

4. The method of claim 2 wherein said compound includes those compounds having $X_1$ as hydrogen, and $X_2$ and $X_3$ are fluorine.

5. The method of claim 3 wherein said compound includes 16 β methyl and 11 β hydroxy.

6. The method of claim 2 wherein said compounds include those compounds having $R_3$ as buterate.

7. The method of claim 2 wherein said compound includes those compounds having $X_1$, $X_2$, and $X_3$ as fluorine.

8. The method of claim 1 wherein said angiogenesis is inhibited by the propionic ester of 4, 6α, 9α-trifluoro-11β, 17α-hydroxy-16β-methyl 3-oxoandrosta-1,4-diene-17β carboxylic acid.

9. A method for treating granulomatous disease in mammals comprising administering a therapeutically effective amount of the compound of claim 1.

10. A method of contraception in mammals comprising administering a therapeutically effective amount of the compound of claim 1.

* * * * *